United States Patent [19]

Calzi et al.

[11] 4,168,294

[45] Sep. 18, 1979

[54] INSTRUMENT FOR PHOTOMETRIC ANALYSES

[76] Inventors: Claudio Calzi, Via Popoli Uniti 8, Milan, Italy, 20125; Alberto Musetti, Vle. Lombardia 28, Milan, Italy, 20131; Adriano Trisciani, Via Marco Praga 22, Monza, Italy, 20059

[21] Appl. No.: 796,867

[22] Filed: May 16, 1977

[30] Foreign Application Priority Data

Feb. 14, 1977 [IT] Italy ............................... 20255 A/77

[51] Int. Cl.² ..................... G01N 33/16; G01N 21/24
[52] U.S. Cl. ...................................... 422/68; 422/81; 422/102; 356/440; 356/246
[58] Field of Search ................. 23/230 R, 253 R, 259; 356/246, 201; 422/68, 63, 81, 102

[56] References Cited

U.S. PATENT DOCUMENTS

| | | | |
|---|---|---|---|
| 3,477,822 | 11/1969 | Hamilton | 23/253 R |
| 3,497,320 | 2/1970 | Blackburn et al. | 23/253 X |
| 3,748,044 | 7/1973 | Liston | 23/253 X |
| 3,811,780 | 5/1974 | Liston | 356/246 X |

*Primary Examiner*—R. E. Serwin
*Attorney, Agent, or Firm*—McGlew and Tuttle

[57] ABSTRACT

Instrument for analyzing, by means of photometric measurements, precisely metered quantities of samples, such as serum, plasma, cerebro-spinal liquid and the like, homogeneously diluted in selectively prechosen reagents.

14 Claims, 11 Drawing Figures

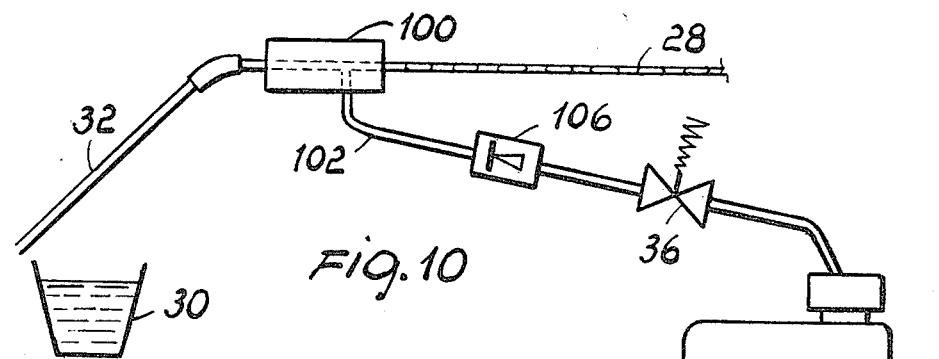
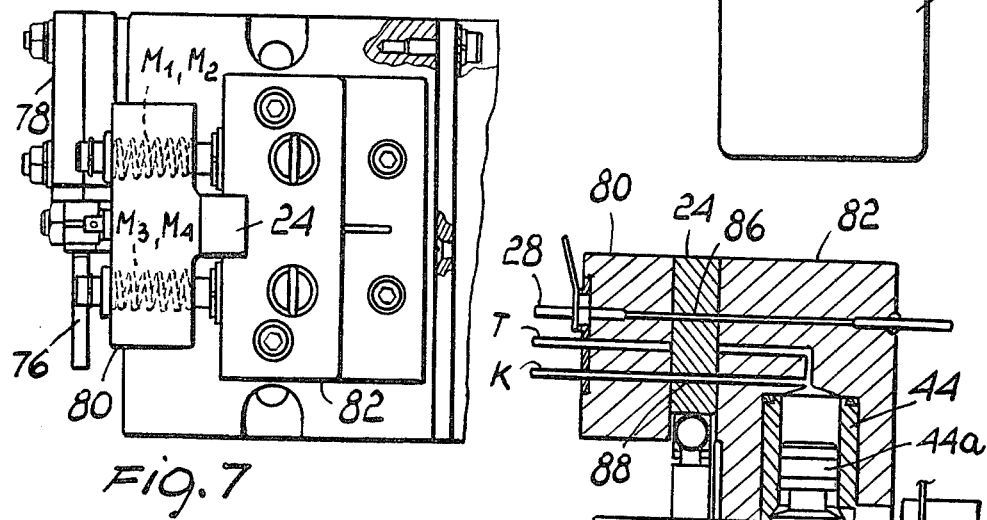
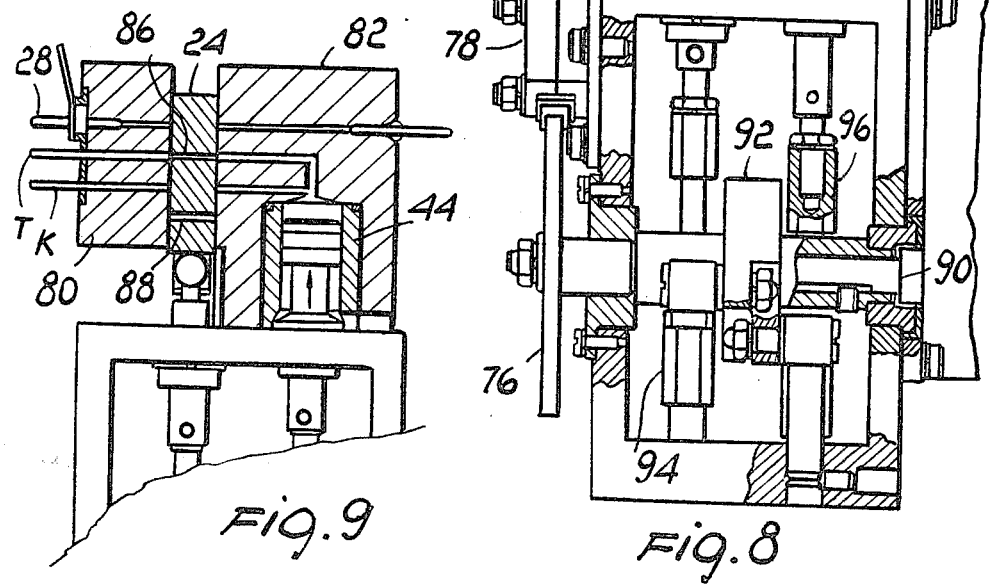

INSTRUMENT FOR PHOTOMETRIC ANALYSES

SUMMARY OF INVENTION

The present invention relates to an instrument for analysing, by means of photometric measurements, precisely metered quantities of samples, such as serum, plasma, cerebro-spinal liquid and the like, homogeneously diluted in selectively prechosen reagents.

Generally, analysis devices using photometric measurements basically operate on the concept of disposing precisely metered quantities of samples (serum, plasma, cerebro-spinal liquid and the like) homogeneously diluted in selectively prechosen reagents, in a transparent container (hereinafter known as a "cuvette" for reasons which will become evident), then passing a light beam, suitably filtered to obtain a monochromatic light of predetermined wavelength, through the cuvette and its contents and concentrating the emerging light beam on to a transducer, such as a photodiode arranged to emit an electrical signal proportional to the intensity of the light striking it.

The light intensity varies with time as the sample reacts with the reagent, and a measurement of this variation is obtained over a predetermined time.

By suitably processing the electrical signal thus obtained, a qualitative and quantitative indication is given of the presence of particular substances for clinical purposes contained in the sample in the described solution, such as glucose, urea and creatinine.

Of all the chemical clinical analyses carried out for illness diagnosis purposes, the majority have been done by colorimetric methods because of the relative simplicity of the instruments necessary for this purpose.

Researchers have therefore been under pressure to study and develop methods requiring the use of this technique.

Initially, the stages of the operation were all manual, and began by proportioning the sample and reagent and then mixing them, after which the incubation stage took place at a perfectly controlled temperature which in the majority of cases was 100° C., and in which the colour completely developed.

The reacted mixture was then poured into a photometric cuvette in which the light intensity or absorbency was measured.

Calculations had then to be made referring the absorbency or light intensity of the analysed samples to that of a reference standard taking account at the same time of any corrections due to the blank.

(The term "blank" signifies a light intensity value deriving from an interfering substance which has to be subtracted from the total light intensity to give the change in luminous intensity deriving solely from the substance under examination).

As technology progressed and the demand for analyses increased, an increasing number of manual operations were automated, so reducing the possibility of human error and at the same time producing an analysis speed which was formerly unthinkable.

Simultaneously the clinical chemical methods evolved, becoming more refined, with increases in accuracy, until the stage was reached of using enzymes where possible, which give the present maximum reaction specificity.

Enzymes enabled reaction temperatures to be used (25° C.-37° C.) which are much easier to obtain and control.

Most existing automatic instruments take the sample, proportion the sample and reagent, mix, incubate (5 minutes-15 minutes), and photometrically read the light intensity or absorbency which in general in compared to an initial calibration made directly by the operator.

The time from presentation of the sample to the instrument to obtaining the data varies from 5 to 15 minutes or more.

Thus, although these instruments are very fast in executing a series of samples, they are not fast in presenting the data, and their limitations are evident when they have to be used in an emergency where the analysis of a single sample is required at one time and immediately.

On this basis, the significance of the instrument according to the present invention is evident, the instrument besides giving a good analysis rate, which is useful in analysing a large number of samples, is at the same time very adaptable, and particularly so in an emergency.

This is so because of novel chemical methods employed which enable the entire incubation period to the omitted.

In this respect, the instrument according to the invention measures variations in light intensity or absorbency over a predetermined period of time, i.e., it does not wait until the reaction has terminated but measures the velocity of reaction instead over a precise given period of time.

In essence, the information required is available after only 45 seconds from the moment of intake of the sample. The data is immediately usable because of the facility for auto-calibration, available at any moment.

This is also made possible by the absolute reproducibility of the system for proportioning the sample and reagent.

The instrument according to the invention uses among other things certain devices and open top containers or cuvettes of transparent upwardly divergent frusto-conical walls and of vertical axis, which have already formed the object of other previous Italian patent applications by the same applicant on July 29, 1974 under No. 25,673 A/74 and Sept. 24, 1975 under No. 27,571 A/75.

The instrument according to the invention is characterised by at least three analyser systems each of which comprises one of said cuvettes and a photodiode, at least four dispensers connected by thin tubes to the cuvettes, and an electronic micro-processor provided with auto-calibration and a digital indicator system.

Each dispenser, of original type, comprises a distributor operated by a reduction motor and is connected in series to other dispensers by a conduit connecting together an initial test tube, the various dispensers and a final collection container, this latter associated with a suction pump via a solenoid valve.

Inlet, outlet and auxiliary sensors (this latter downstream of the outlet sensor) are also provided for feeding electrical signals, by means of suitable circuits, to the micro-processor which is arranged to emit a signal for initiating the analysis cycle and controlling a solenoid valve to stop the intake of the sample.

Each dispenser also comprises a small syringe connected at one end to its respective distributor and at the other end to a container of reagent to be fed with the sample into the cuvettes.

The thin tubes carrying the sample and reagents to the cuvettes are also arranged to carry a stream of air and a suitable wash liquid.

Thus with the instrument according to the present patent application, continuous accurate analyses may be rapidly and automatically made by photometric measurements, of even minimal proportioned quantities of different samples of serum, plasma, cerebro-spinal liquid and the like without encountering appreciable phenomena of alteration or crossed contamination.

DESCRIPTION OF THE DRAWINGS

One preferred representation but not exclusive embodiment of the invention is shown in the accompanying drawings, in which:

FIG. 7 is a view of a dispenser from above;

FIG. 8 shows one of the dispensers, partially in lateral view and partially as a section on a vertical plane containing the mechanical devices for the selection and change-over of the passages and metered feed of the reagent;

FIG. 9 is a fragmentary view of the device of FIG. 8 in another of the positions assumed thereby during the respective operating cycle;

FIG. 10 is a diagrammatic representation of the wash device for the apparatus;

DESCRIPTION OF PARTICULAR EMBODIMENT

Figure 1:
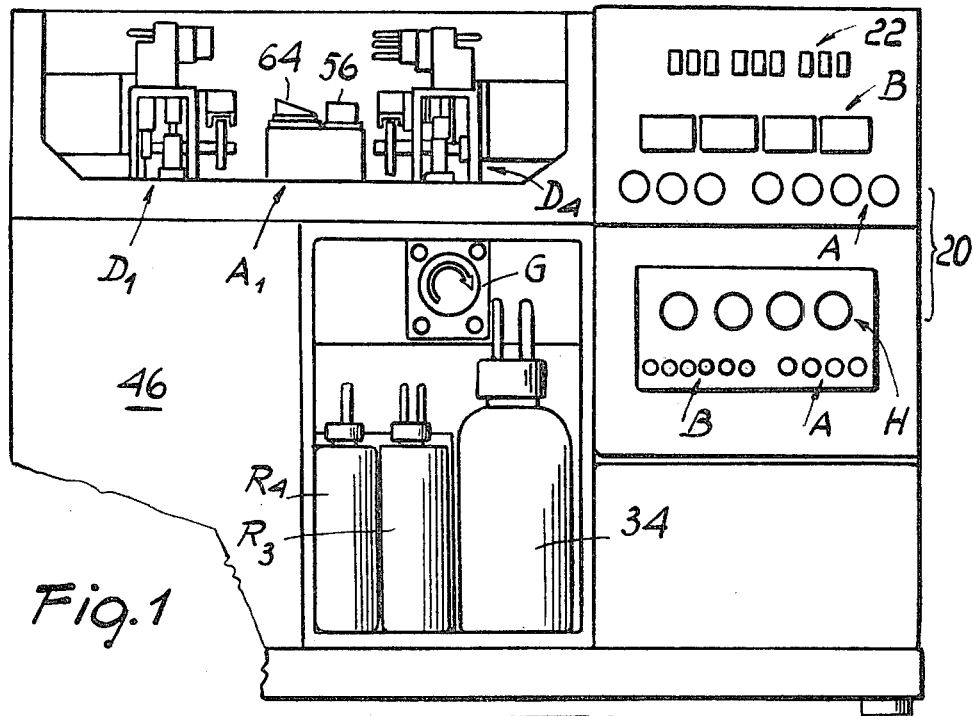
FIG. 1 is an essentially diagrammatic frontal elevational view to a small scale, of the apparatus according to the invention, part of the front walls being removed to enable the position of certain assemblies, components and removable containers to be seen.

In the embodiment shown in FIG. 3, the actual operational assembly, contained within a dashed and dotted line 10, comprises for example three analyser systems A1, A2, A3 each including a respective cuvette C1, C2, C3 designed to contain the sample with the reagent for a predetermined time forming part of an operational sequence or cycle hereinafter described, and arranged to be rotated in accordance with a predetermined cycle by a motor 12 which drives all the cuvettes, for example via a drive belt 14.

These cuvettes, diagrammatically indicated in FIG. 3 in a position turned through 90° from their effective position (to show their contents and their association with the feed circuits described hereinafter) belong to structurally identical assemblies, only one of which has been shown in the figures which follow, and will be described in detail.

By means of thin tubes T1, T2, T3, these cuvettes are connected to a like number of dispensers D1, D2, D3, also described hereinafter.

The cuvette C3 is connected selectively by a tube T4 to a fourth dispenser D4, to enable other alternative analysis processes to be executed in this cuvette.

The cuvettes are located and oriented in such a manner that they may be each traversed by a light beam suitably centred and focused and produced by a lamp or light source 16, and which after passage through an optical filter reaches a respective photodiode F1, F2 and F3, the output of which is fed through a respective circuit 18 to an electronic micro-processor 20, the outputs from which are in their turn fed to indicating means such as digital displays belonging to a visual indicator system 22 (possibly a memory or recorder) which gives the results of the analysis.

Thus, in the embodiment shown, the assembly heretofore described enables three different distinct indications to be derived from the photometric analysis carried ourt in each of the analysers A. However the device may comprise a different number of analysers each supplied through its own channel and each with its own processor and a distinct indicator means. Different means may be used with different connections for carrying out alternative processes, for example two analyses may be carried out in the cuvette C3 using the dispenser D3 or dispenser D4, at the choice of the operator.

To obtain various analysis results from a single sample, metered fractions of said sample are fed into the individual analyser cuvettes C together with metered quantities of different reactants. The metering, feed and mixing stages form the initial part of the aforementioned cycle, this part requiring the operation of the respective dispensers.

Figure 3:
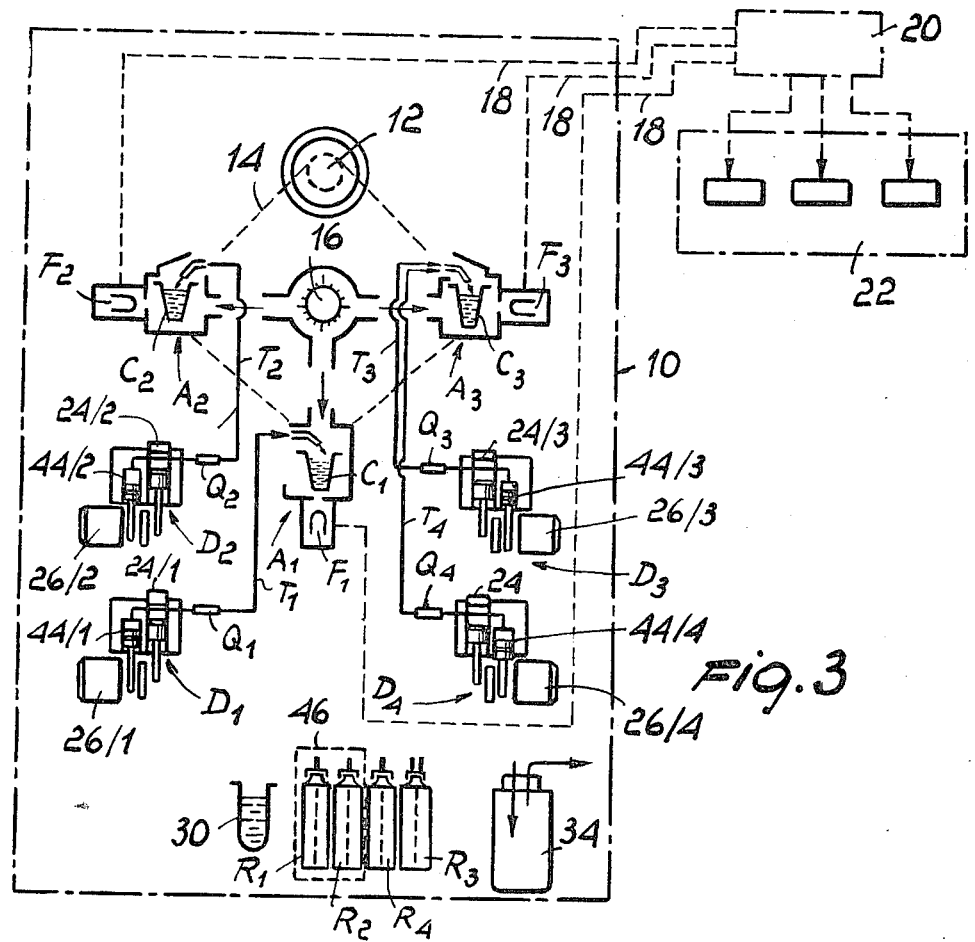
FIG. 3 is a diagrammatic representation of the association of the mechanical, electrical, photoelectric and electronic devices which directly cooperate for simultaneously executing a plurality of different analyses on the same sample.
Figure 3A:
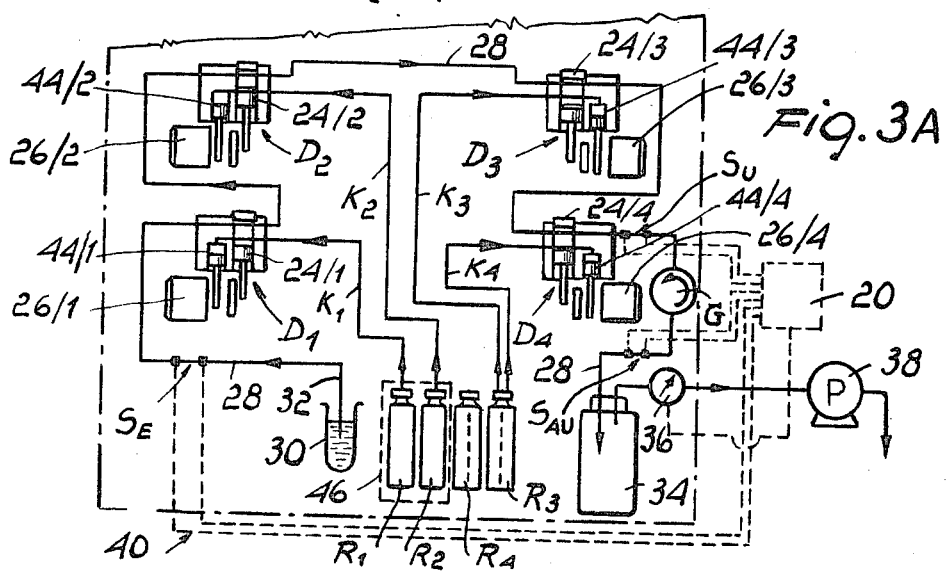
FIG. 3a is a partial view of the same diagram in the preparatory stage of feeding the mixture (as yet not homogenised) of the sample selectively associated with various reagents, into the cuvettes for the purpose of executing the photometric analysis process.

These stages, which terminate with the preparation of the homogeneous mixtures of the sample and respective reagents in each individual cuvette, are generally evident from FIG. 3A.

The dispensers, described in detail hereinafter, each comprise a particular distributor 21/1-24/4 which, driven mechanically by a respective reduction motor 26/1-26/4, has the double purpose of temporarily forming a small portion of a conduit 28, of very small exactly predetermined volume, which travels across all the dispensers in series, starting from the container which for example is a test tube 30 and in which the sample to be analysed is disposed and presented to a dipping needle or tube 32 forming the inlet to said conduit 28 and terminating in a collection vessel 34 connected via a solenoid valve 36 to a suction pump 38 arranged to create a vacuum in said vessel 34 sufficient to draw the sample through the conduit 28, thus filling each of said short portions 24/1-24/4 of the distributors belonging to the respective dispensers D1-D4.

The saturation or filling of all the portions 24/1–24/4 is attained as a consequence of the saturation or filling of the entire conduit 28.

The attainment of this saturation is indicated by suitable sensors each formed by a portion of this conduit defined upstream and downstream by electrically conducting parts, between which a potential difference is applied.

If the liquid, which is sufficiently conductive, is present then its existence in the parts forming said sensors is indicated. The device comprises an inlet sensor SE upstream of the first dispenser D1, and at least one outlet sensor SU downstream of the last dispenser D4.

For certain special processes, the device also comprises an auxiliary outlet sensor SAU disposed downstream of the outlet sensor SU.

These sensors feed electrical signals by way of suitable circuits or lines 40 to a micro-processor 20 which in its turn emits and initiation signal for the analysis cycle and which, among other things, also controls the solenoid valve 36 so as to stop the sample being drawn into the conduit 28.

The sensor SE operates on the basis of an automatic cycle (obtained by associating suitable automatic devices and controls) to determine the quantity of liquid drawn in, this quantity being defined on reaching the sensor SE.

Said dispensers D1–D4 also each comprise a small syringe 44/1–44/4 which becomes temporarily connected via the respective distributor 24/1–24/4 and tube K1–K4 to the respective vessels R1–R3 (K3 and K4 both flow out of R3) for the reagent to be fed, together with the respective metered quantity of sample, to the cuvette C1–C3.

These syringes 44/1–44/4 are also driven by the respective reduction motor 26/1–26/4 of the individual dispensers D1–D4.

The reciprocating movement of the syringes 44/1–44/4, suitably synchronised and in phase with the other operations of the device, causes a small quantity (volumetrically determined by the capacity of the syringes, for example 650 microliters) of the different reagents to be drawn into the respective dispensers D1–D4.

On termination of these preparatory stages, the controlled movement of the distributors 24/1–24/4 brings the dispensers D1–D4 into the position shown diagrammatically in FIG. 3 (the constructional details of the dispensers D1–D4 and the manner in which they operate will be described in greater detail hereinafter).

In this position, the syringes 44/1–44/4 are connected to the respective tubes T1–T4 via the same portion formed by the respective distributor 24/1–24/4, into which a quantity of sample has been previously introduced.

The "thrust" stroke of the syringes 44/1–44/4 feeds a liquid column into the cuvettes C1–C3 a liquid column (of quantity determined by the characteristic volume of said syringes) which runs through the respective tube T1–T4 along with which there is the small metered quantity of sample, which has been previously introduced into this portion of the respective distributor 24/1–24/4.

In FIG. 3, these small quantities, indicated by Q1–Q4, and 4, 2, 40 and 4 microliters respectively, are diagrammatically indicated by short thickened lines at a point along the length of the respective tubes T1–T4 to make the operation of the dispensers more evident.

Consequently, on termination of the mechanical operations carried out by the dispensers D1, D2 and D3, or alternatively D4, the various cuvettes C1–C3 contain (after previous heating) said small respective quantities Q1, Q2 and Q3, or alternatively Q4, together with the respective reagents R1, R2 and R3 in the quantities metered by the reciprocating suction and delivery movement of the syringes 44/1–44/4.

In subsequent manipulation stages for quantities, the sample quantities are perfectly mixed with the quantities of the respective reagent inside the analysers A1–A3.

This mixing takes place by rotation of the cuvettes C1–C3 at a speed of 700 r.p.m., controlled electronically by the micro-processor 20. (The motor 12 provided with a tachometer generator arranged to feed a signal to the processor 20 proportional to the motor speed).

The direction of rotation imparted by the motor 12 to the cuvettes C1–C3 alternates from clockwise to counter-clockwise, to aid mixing of the liquid in the cuvettes.

The mixtures thus obtained undergo change in optical density with time, this variation being detected by the photodiodes F1–F3 and fed to the micro-processor 20 which supplies the required analysis results, either visualised or otherwise quantified by the indicator device 22.

The device described in general terms above can of course be integrated with other auxiliary means, such as:

For example, the reference numeral 46 diagrammatically indicates the manner in which at least part of the vessels R1–R3 for the reagents may be disposed and maintained in a separate environment, in particular a refrigerated environment, to preserve reagents which may alter with heat.

Where only very small quantities of physiological sample are available (for example in the chemical field or in pediatric diagnosis), the system for saturating the conduit 28 by means of suction in the vessel 34 may be replaced by a manual intake system, for example by a manually operated peristaltic pump G, so as to visually check that the sample reaches, in the necessary minimum quantity, the metering portion or portions selectively present in one or more of the distributors 24/1–24/4.

Moreover, complete wash cycles are interposed between successive analysis cycles on different physiological samples, for the entire length of the conduit 28 in its continuous condition as diagrammatically indicated in FIG. 3A by running therethrough a stream of air and/or suitable wash liquid contained in R4, utilising the vacuum present in the container 34 and by immersing dipping needle 32 into container R4. According to an important characteristic of the invention, the wash cycles are supplemented by a particularly intense elimination of all traces of the reagent and samples present in the cuvettes by causing the cuvettes C1–C3 to temporarily rotate at high speed, for example of the order of 6000 r.p.m., by the said motor 12. The motor 12 with belt 14 form drive means for the cuvette. This enables the apparatus to operate continuously when sequentially analysing different successive samples, by preventing any danger of cross-contamination.

Figure 4:
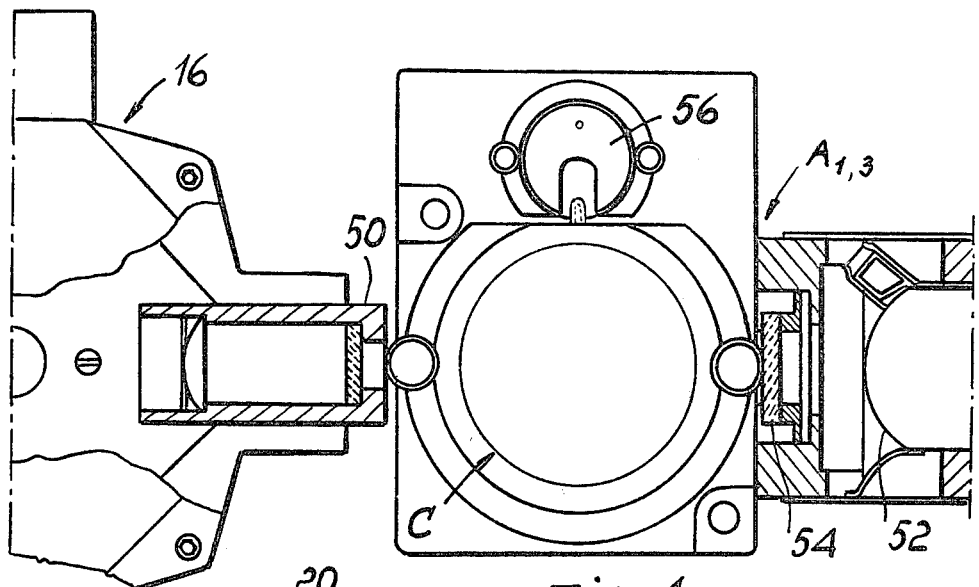
FIG. 4 is a fragmentary diagram to a greater scale of the light source and one of the cuvettes, partially as a view from above and partially as a section taken on a horizontal plane containing the optical axis.
Figure 5:
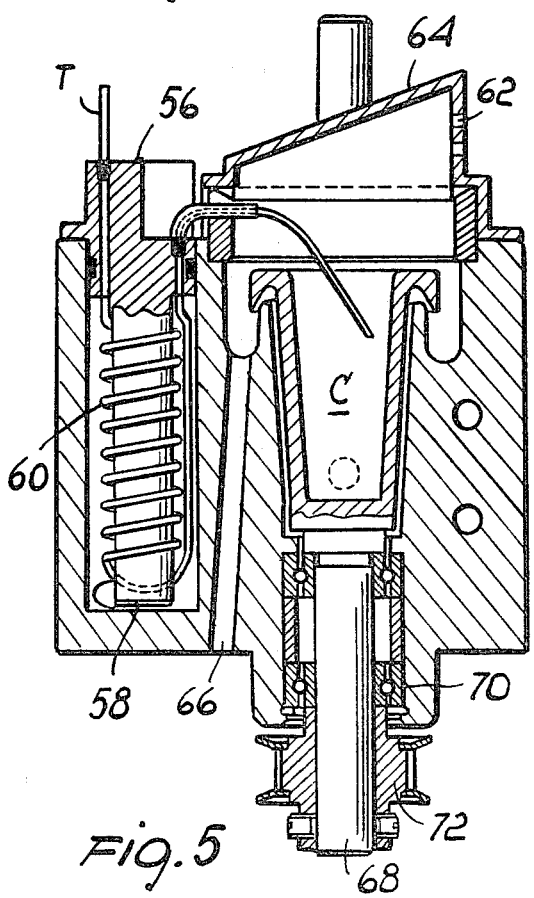
FIG. 5 is a section through the same (or any other) cuvette on a vertical plane containing the axis of rotation thereof.

The centrifugal force developed by this rotation completely evacuates the liquid, composed of the reagent and sample, from the cuvettes C1–C3 (see FIG. 5) and forces it into the conduit 66 from whence it leaves by gravity to the outside through a suitable hole and is collected in a waste bottle (not shown). To permit this rotation, cuvettes C are symmetrical about their vertical axis as is shown in FIGS. 4 and 5.

Examining the various accompanying figures in detail, FIG. 1 shows the instrument overall, mounted on a base on the right of which (with reference to the figure) are the micro-processor 20, the operator's controls A and H, the signals B indicating the particular stage of operation of the machine, and the numerical display indicators 22. The left hand side comprises a reagent container R3, the wash liquid container R4 and refrigerated portion 46, the vacuum bottle 34, the peristaltic pump G, two dispensers D1 and D4 and an analysis station A1.

Figure 2:
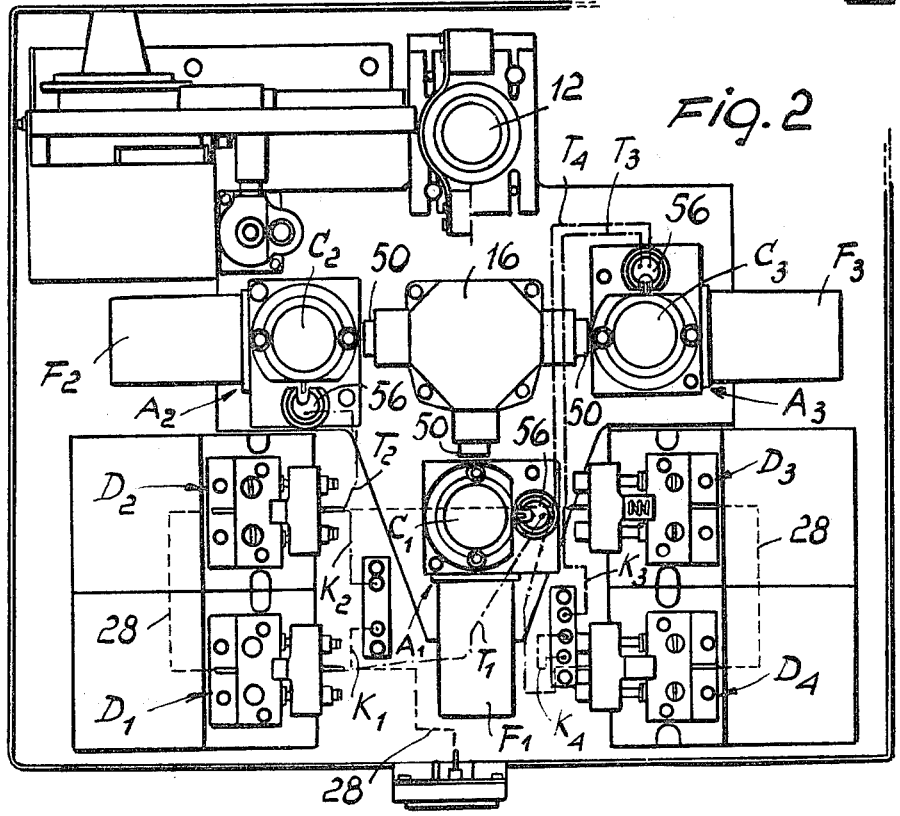
FIG. 2 is a more detailed plan view of the assembly comprising the various feed, drive and control mechanisms for the cuvettes and the photometric analysis means.

FIG. 2 shows the dispensers D1-D4, the analysis units A1-A3 with their respective cuvettes C1-C3 and photodiodes F1-F3, the motor 12, the lamp 16 with three lenses 50 and the recirulation and heating circuit 56 for heating water for the units A1-A3.

FIG. 3 shows the units A1-A3 and the members shown in FIG. 2 with the exception of the heating water circuit 56, and also shows the electronic devices, such as the micro-processor 20 and the visual indicator system 22.

FIG. 3A shows the various members concerned in feeding the sample-reagent mixture into the cuvettes, including the sensors SE, SU, SAU. The operation of these sensors is as follows.

SE and SU are used when the instrument functions automatically. This occurs in practice when an automatic sampling plate on which various test tubes 30 containing different samples are disposed, is connected to the instrument.

In this case a needle 32 (see FIG. 10) is automatically introduced into the test tube 30 disposed on a rotating plate (not shown), and the instrument aspirates the sample through the needle 32 to the sensor SE. At this point, this latter feeds a signal to the processor 20 which causes the needle 32 to rise from the test tube 30 by means of a device (not shown) disposed on the automatic sampling plate. Consequently, the needle draws in air and the sample moves from SE through the path 28 to SU.

On reaching SU, suction is terminated by the changeover the solenoid valve 36, and a signal is fed to the processor 20 for initiating an analysis cycle.

That portion of the sample lying between D3 and SU not used for analysis serves for washing the conduit 28 free of traces from previous samples.

Any residues remaining from the previous analysis contaminate this initial portion of the sample, but not the part fed to the cuvettes.

The automatic operation of SE and SU is heretofore described, but SU also operates manually, in which case the sample is presented directly to the analyser without activating SE, and SU informs the processor 20 when the conduit 28 is saturated with sample to be analysed.

SAU carries out the same function as the sensor SU, and therefore operates either manually or automatically each time the dispenser D4 is activated, but allows a greater quantity of sample (for example urine) to be introduced into the conduit 28 so as to improve the washing of the conduit.

In this case, the sensor SU is electrically de-energised and that part of the sample to be used for washing occupies the portion of the conduit 28 from D4 to SAU (greater than from D3 to SU), while the rest of the sample to be used for analysis occupies the remaining portion of the conduit 28.

FIG. 4 is a detailed view of an analysis unit A and a portion of lamp 16 and optical condenser and thermal filter 50, the unit showing the cuvette C, the photodiode 52 with the optical filter 54 and a preheater 56 for the reagent and sample originating from the tube T (also shown in FIG. 2).

The preheater 56 and cuvette C are more evident in FIG. 5. The preheater 56 consists of a cylindrical support 58 about which a stainless steel coil 60 is wound.

The heating water circulates around this coil.

The reagent and sample are injected into the coil 60 by the dispenser, and the coil is connected to the cuvette which is to be filled.

The cuvette C is covered on top by a cover 62 with an upper inclined surface 64 to allow any condensate, where present, to flow into the discharge channel 66.

The cuvette C extends downwards by a shaft 68 mounted on ball bearings 70 and on which a drive pulley 72 is keyed, connected to the motor 12 by a toothed belt 14.

FIGS. 6, 7, 8, 9 show a dispenser D in its various views and stages of movement.

Figure 6:
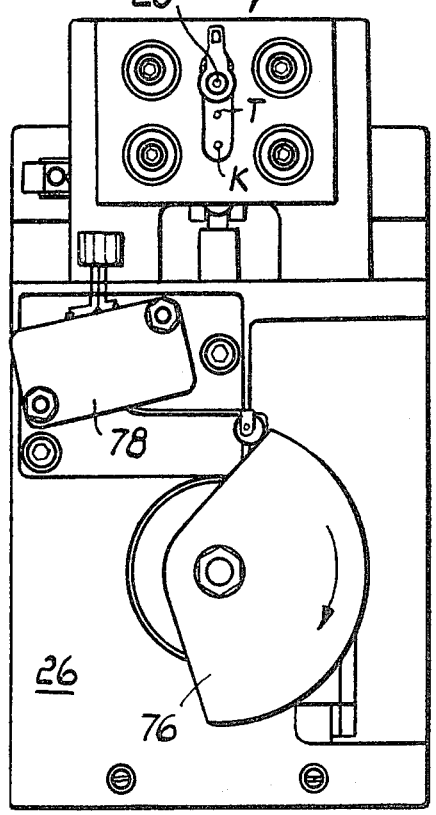
FIG. 6 is a detailed view of a mechanism associated with any one of the dispensers, for determining the operational sequence.

FIG. 6 shows a cam 76 and microswitch 78 which control the commencement of the sample measuring cycle and stop the reduction motor 26 of the dispenser when it has completed its cycle. The cam 76 is keyed on to the reduction motor 26 and this latter is controlled via the processor 20 when the sample reaches sensor SU.

FIG. 6 and the following ones 7 and 8 show the distributor valve 24 comprising a preferably stainless steel parallelepiped block with flat parallel lapped surfaces.

This block is disposed between two jaws 80,82 of preferably plastic material, for instance P.T.F.E. In jaw 80 stainless steel bores are provided for capillary tubes 28, T, K, connected respectively to the path of the sample, to preheater 58 and to the reactive bottle R relating to the channel to which that dispenser belongs. Jaw 82 keeps the block 24 pressed against jaw 80 by means of 4 springs M. Jaw 80, fixed to the body of the dispenser, carries the seat of syringe 44 with the plunger 44a and the bores 28, T, K.

FIGS. 8 and 9 show a section through the distribution block with the valve 24 and jaws 80, 82, and the syringe 44 for the reagent.

The dispenser is shown in one stage of operation in FIG. 8, and in another stage in FIG. 9.

The valve 24 comprises two parallel transverse bores 86 and 88 (FIGS. 8 and 9).

The higher of the two bores, 86, connects the sample inlet to the vacuum vessel 34 when the valve is raised, and forms an integral part of the path 28, while when the valve is lowered it connects the reagent syringe 44 to the cuvette C via the conduit T.

The lower of the two bores, 88, connects the reagent syringe 44 to the reactant bottle R1-R3 via the conduit K when the valve is raised, while when the valve is lowered this bore is not traversed by fluid.

The dispenser therefore has four stages of operation corresponding to 90° rotations of the reduction motor, the shaft 90 of which alternately operates, by means of an eccentric 92 and rollers, the cams 94 and 96 connected to the valve 24 and syringe 44 respectively.

The shaft 90 of the reduction motor operates also the cam 76 acting on the microswitch 78.

It follows that during the first stage, the valve 24 with its bore 86 full of sample moves downwards (see FIG. 9). During the second stage the syringe which was at the bottom is raised to inject into the cuvette the reagent and the quantity of sample contained in the previously lowered upper bore 86. During the third stage the valve returns upwards. During the fourth stage the syringe returns to the bottom to load the reagent.

As stated heretofore, an essential feature of the instrument according to the invention is its capability to execute repeated closely successive analysis cycles on different samples, in particular originating from different patients, without any practical danger of cross contamination of the biological samples.

An important factor in attaining this capability is that the instrument comprises means for ensuring, and is operable in such a manner as to ensure, an effective and practically complete wash cycle between the successive analysis processes for all the conduits, cavities and passages in which the biological fluid analysed during the previous cycle was previously present. In practice this wash is effected by passing a suitable liquid contained in the bottle R4, in particular a wash solution, through the entire path 28 from a point close to the test tube 30 to the discharge vessel 34 connected to the vacuum pump 38 (see FIG. 10).

Improved wash efficiency is obtained by passing a wash solution segmented with air along the same path.

During the analysis process stages, or rather during the preparation leading up to the analysis itself, the needle 32, representing the beginning of the conduit 28, is immersed into the test tube 30 containing the sample, and consequently the sample, drawn in by the vacuum applied to 34, fills said conduit (under conditions controlled by the sensors as previously described).

During the wash stages, the needle 32 is extracted from the test tube 30 (in fact the test tube is withdrawn from the needle) and consequently air is drawn into the conduit 28.

A T connector 100 is disposed in this conduit 28 at a short distance downstream of the needle 32, to connect said conduit 28 to a second conduit 102 originating from a vessel R4 containing the wash solution.

Means are disposed in this branch 102 for closing the connection during the sample suction stage, such as a solenoid valve 36 controlled by the instrument programmer, and/or possibly a fluid diode 106 which enables liquid to move only in the suction direction.

Thus, during the wash stages, the wash liquid (from the container R4) and the air drawn through the needle 32 converge at the meeting point of the passages formed by the conduits 28 and 102 (in the device 100, in which said passages are suitably and proportionally gauged), the interior of the conduit 28 therefore being cleaned of the residues of the sample previously drawn in.

Consequently, the wash liquid associates with the induced air downstream of the device 100, and is distributed along the conduit 28 in the form of a fragmented sequence of short columns of liquid and short columns of air, as shown diagrammatically in FIG. 10 by the short portion of the conduit 28 downstream of the device 100.

Figure 11:
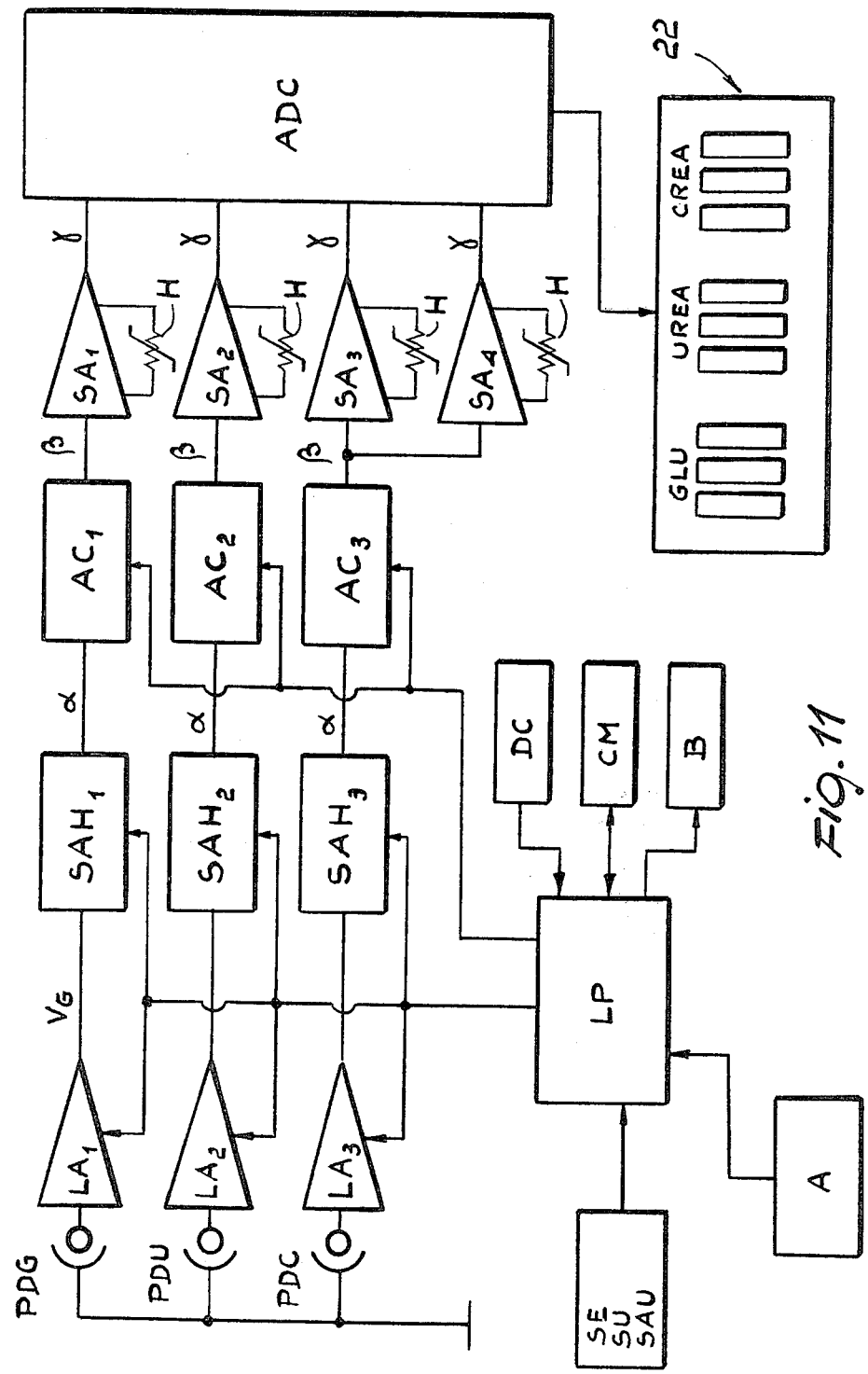
FIG. 11 is a block diagram of the micro-processor and indicators.

FIG. 11 represents the block diagram for the electronic micro-processor included in the part indicated by 20 in FIG. 1 and 3. The portions of the circuit which control the drive means 12, 14 and the dispenser means (D) termed control circuit means and the portions for analyzing the sample are termed analysis circuit means.

Experts of the art can easily deduce the various connections and interlocks from this diagram.

In FIG. 11, the symbols have the following meanings:

| | |
|---|---|
| PDG | Photodiode glucose |
| PDU | Photodiode urea |
| PDC | Photodiode creatinine |
| LA1-LA3 | Logarithmic amplifiers(with automatic zero) |
| SAH1-SAH3 | Analogue memories |
| AC1-AC3 | Auto-calibrators |
| SA1-SA4 | Scale amplifiers |
| H | Amplification controls |
| ADC | Analogue to digital converter |
| SE, SU, SAU | Inlet, outlet and auxiliary outlet sensors |
| A | Front panel keys |
| LP | Logic micro-processor |
| DC | Dispenser control |
| CM | Cuvette motor control |
| B | Front panel indicator lamps |
| GLU | GLucose display |
| UREA | Urea display |
| CREA | Creatinine display |

Glucose, urea and creatinine testing is effected by means of photometric measurements. In each cuvette are introduced metered quantities of sample and reagent, and after stirring, the current $I_0$ which is an analysis signal, of the photodiode is measured at instant $t_0$, said current being proportional to the optical density of the solution contained in the cuvette.

After a time interval $\Delta t$, that is, at instant $t_1$, a new measurement is made: $I_1$ being the current measured; such a current is different from $I_0$ because in the meantime the optical density of the solution is changed.

The current values measured depend from the Lambert-Beer Law:

$$I_1 = I_0\, e^{\,KC(t_1-t_0)}$$

where: K is the extinction coefficient, known and typical of the reaction; C is the concentration of the substance (for instance, glucose) in the solution; by knowing $I_1$; $I_0$ and $\Delta t$ it is possible to obtain concentration C, by means of the equation:

$$c = \frac{1}{K(t_1 - t_o)} \lg \frac{I_1}{I_o} = \frac{1}{K\Delta t} \lg \frac{I_1}{I_o}$$

The data processing process schematically shown in FIG. 11 is described in the following for sake of clarity only as far as glucose is concerned, but obviously it may be applied also to other tests.

The signal coming from photodiode PDG reaches logarithmic amplifier $LA_1$, also capable of storing $I_0$ and of using said current as a reference for logarithmic conversion according to equation:

$$V_u = \text{cost} \cdot \lg \frac{I_1}{I_0} = \text{cost}' \cdot c\Delta t = \text{cost}'' \cdot c$$

where a constant interval $\Delta t = t_1 - t_0$ has been considered.

Therefore, at the outlet of $LA_1$ there is a voltage $V_u$ proportional to $I_1$ and thus to the glucose concentration in the solution.

Said voltage is stored in circuit $SAH_1$ and it is found at point $\alpha$ in FIG. 11.

After point $\alpha$ an automatic calibration circuit is placed, provided so that by pressing one of push buttons A and by presenting at the inlet of the instrument a standard one, the amplification factor of $AC_1$ varies in such a way that at point $\beta$ in FIG. 11 there will be a voltage having a fixed value.

The amplifier $SA_1$ is used to correlate by means of potentiometers H, said voltage value to the glucose content in the standard itself and supplies at the outlet at point $\gamma$, a voltage $V_G$. ADC is a 4 channel analogue-digital converter which transforms voltage $V_G$ in binary value visualized by display 22.

For instrument economy the creatinine values in serum and in urine, correlated to channels $SA_3$ and $SA_4$ are presented on the same display controlled by the operator. The logic microprocessor LP has the function of supervising all the steps of the various operations.

By way of example a cycle of manual operations is described.

The operator presents the sample to the suction needle 32 and presses a push-button A. This causes suction of the sample in conduit 28 until $S_u$ is reached. At this point suction is stopped and dispensers D are actuated.

When each dispenser has injected in the respective cuvette the reactive and sample mixtures, cams 76 of FIG. 6 are rotated by about 180° and trip microswitches 78 signalling to the logic processor to start mixing. In the meantime a timer inside the logic processor is actuated, which, besides carrying out the washing step through device 102, indicates storage times $t_0$ and $t_1$ of value $I_0$ $I_1$, indicates the end of cycle at the time $t_1$, by providing for discharge of the test tubes through quick rotation of motor 12, thus preparing the instrument for the next testing operation.

The logic micro-processor also comprises circuits capable of moving only the selected dispensers D and of instantaneously stopping the dispenser motors when cam 76 is rotated by 360°, by returning the dispensers to the original position.

Other functions of the logic micro-processor are:
to actuate self-calibration circuits;
to collect signals from sensors and taking into account the selections made on front panel A;
to supply guide indications for the operator through the front luminous panel B.

The description given heretofore relates to a preferred embodiment of the instrument according to the invention.

However, the instrument can obviously undergo various modifications both in its constructional details and in the individual devices included therein, without leaving the scope of the inventive idea, in accordance with specific requirements of service convenience, manufacture, installation and association with other complementary instruments, devices and equipment designed in particular for the complete automation of the analysis cycle sequences.

For example, and without constituting a limitation on the invention, experts of the art will observe that an instrument according to the invention could comprise a different number of cuvettes and dispensers (from one upwards).

The cuvette dimensions (0.1 to 10 cm of optical path, preferably 1 cm) could be different.

Likewise, the dispensers and the associated means which determine the metering of the sample (conduit portions 86 in the valve 24, FIGS. 8 and 9) and of the reagent (syringes 44, FIGS. 8 and 9) are dimensioned according to convenience.

For example, the instrument may be set for analysing two microliters in the case of the urea, four microliters for the glucose in the serum or cerebro-spinal fluid, forty microliters for the creatinine in the serum and four microliters for the creatinine in the urine, in 0.65 cm³ of reagent. These values may obviously vary over a wide range, as may the types of reagent (not forming a characteristic of the invention).

Similarly, the termal treatment conditions, as determined by the heaters 56 (FIGS. 4 and 5) may be varied between freezing and boiling point, a temperature close to the natural physiological temperature, of the order of 37° C., being obviously preferred.

From the constructional aspect, the materials used for manufacturing the dispensers, cuvettes, etc. may be modified, as may the specific technical and geometrical designs for their construction.

Other individual devices may be replaced by other equivalent devices or even omitted (for example the fluid diode 106 of FIG. 10), and the pump 38 of FIG. 3A may be of peristaltic type instead of vacuum type.

The sensors may be of optical or thermal type, and the electronic assembly may be modified in accordance with various requirements, so that it operates in accordance with a desired system, incorporating auto-calibration together with automation of the various operating sequences, all without leaving the scope of the invention.

What we claim is:

1. An instrument for analyzing, by means of photometric measurements, precisely metered quantities of essentially liquid samples of physiological origin which are diluted in selectively prechosen reagents, by photometrically determining optical density variations of the sample-reagent mixture at predetermined light frequencies over a predetermined time period, comprising, at least one cuvette arranged to contain a sufficient quantity of the mixture in a position in which said quantity may be traversed by a filtered light ray, said cuvette having a vertical axis of symmetry and enclosing a containing cavity of cone frustum walls diverging upwards, said cuvette mounted for rotation about said axis, rotary drive means connected to said cuvette for applying a sequence of rotary movements to complete a mixing of the mixture in said cuvette, and to totally expel the mixture on termination of the analysis, at least one light source associated with concentrating optical lens systems for transmitting light rays through said mixture present in said at least one cuvette, to reach corresponding analysis photodiodes, at least one dispenser-metering device for sequentially feeding metered quantities of sample and reagent into said respective cuvette, and a programmer and control assembly for sequentially operating means for driving said cuvette and dispenser-metering devices for executing the cycle.

2. An instrument as claimed in claim 1, including a wash system in which the passages, conduits and cavities traversed by said mixture are likewise traversed by a wash solution, said wash system comprising a segmented column in which short columns of said solution are alternated with air bubbles, in the intervals between the analyses cycles, the operation being obtained by drawing air and wash solution through a T connector.

3. An instrument as claimed in claim 2, comprising suction means for alternately drawing in the samples and wash solution to be fed to the dispenser-metering device, for obtaining the metered quantities of said samples and for washing respectively.

4. An instrument as claimed in any one of claim 3, comprising dispenser-metering devices including inlets for the samples and for the reagent and diluent respectively, a slide valve comprising two passages which in one position connect the sample inlet to a suction means for said sample, and the reagent inlet to a drawing and pumping syringe, the first passage constituting a small metering space in which there is present a metered quantity of the sample under suction conditions, while in a second valve position said first passage becomes positioned along a conduit joining said syringe said cuvette, so that said syringe, in its compression and delivery stage, feeds the reagent and diluent drawn into it into said conduit together with the metered quantity of sample present in said small cavity, and which therefore becomes dispersed and mixed in said feed conduit to the analyser.

5. An instrument as claimed in claim 4, wherein the rotary drive means for the analyser cuvettes are arranged to carry out a preliminary relatively slow reciprocating rotation stages for completing dispersion and mixing of the metered sample in the metered reagent and diluent.

6. An instrument as claimed in claim 5, wherein said drive means impose a final rapid rotation stage on said cuvettes for centrifugally removing the sample-reagent and diluent mixture on termination of the photometric analysis stage.

7. An instrument as claimed claim 3, wherein said suction means include a peristaltic pump for manually drawing the samples into said dispenser-metering device.

8. An instrument as claimed in claim 1, wherein said programmer and control assembly comprises electronic means for auto-calibrating values received at each stage of analysis, for setting to an original value prior to the execution of a subsequent analysis stage or cycle.

9. An instrument as claimed in claim 4, wherein the conduit traversing the dispenser-metering means for feeding the sample through the metering space contained therein includes sensors, said dispenser-metering device comprising a plurality of dispensers along said conduit, said sensors disposed upstream of a first dispenser and downstream of a last dispenser, for indicating the presence of said sample one of said dispensers or in each of said dispensers, the programmer and control assembly being interlocked with consent controls constituted by signals emitted by said sensors.

10. The instrument for analyzing physiological liquids comprising:
(a) at least one cuvette having a vertical axis of symmetry and mounted for rotation about said axis, said cuvette having one cavity with a frusto-conical shaped side wall diverging upwardly and symmetrical about said axis for containing a liquid sample;
(b) drive means connected to said at least one cuvette for rotating said cuvette about said axis at various speeds and in a forward and reverse direction;
(c) at least one sample container for the physiological liquid to be analyzed;
(d) at least one reagent container for a selected reagent to be mixed with the physiological liquid to form a reacting mixture;
(e) dispenser means associated with said sample container, reagent container and cuvette for dispensing a metered quantity of physiological liquid and reagent into said cuvette to form the reacting mixture;
(f) control circuit means connected to said drive means and dispenser means for controlling said dispenser means to dispense the reacting mixture into said cuvette to drive said cuvette at a first mixing speed in at least one of a forward and reverse direction to mix the reacting mixture and to drive said cuvette at a second higher speed to expel the reacting mixture from said cuvette by centrifugal force acting on the mixture to drive it upwardly along said frusto-conical shaped wall and out of the top of said cuvette;
(g) said cuvette including at least a portion transparent to light radiation;
(h) a light source for shining light through said transparent portion of said cuvette associated with said cuvette;
(i) a photosensor associated with said light source for receiving the light shined through said transparent portion of said cuvette and for producing an analysis signal corresponding with the shined light which varies as the mixture reacts;
(j) analysis circuit means connected to said photosensor for receiving the analysis signal and comparing the level and variation of the analysis signal with levels and variations for known physiological liquids to analyze the sample; and
(k) digital display means connected to said analysis circuit means to display the results of the analysis.

11. An instrument according to claim 10, further including a sample conduit extending from said sample container, said dispenser means comprising a valve block having opposite flat parallel surfaces with at least two passages therethrough extending between said two surfaces, first and second jaw members disposed on either side of said valve block each having flat surfaces engaged with said flat surfaces of said valve block, said sample conduit extending through said first and second jaw members, said passages of said valve block comprising a sample passage having a precisely preselected volume for the sample to be analyzed, and a mixture passage, a reagent conduit extending from said reagent container, a mixture conduit extending from said dispenser means to said at least one cuvette, a syringe having a seat in said second jaw member and a plunger slidable within said seat, said first jaw member including portions of said reagent conduit and said mixture conduit and said second jaw member including portions of said reagent conduit and mixture conduit aligned with said former mentioned portions of said reagent conduit and said mixture conduit in said first jaw member, said portion of said reagent and mixture conduits in said second jaw member extending from said flat surface of said second jaw member to said seat of said syringe, said valve block being slidable from a first position wherein said sample passage is aligned with said sample conduit extending through said first and second jaw members and said mixture passage aligned with said reagent conduit extending through said first and second jaw members, and to a second position wherein said sample passage is aligned with said mixture conduit extending through said first and second jaw members, and motor means connected to said syringe plunger and said valve block for moving said valve block between said first and second positions and for sliding said plunger into and out of said syringe seat, and sample pump means connected to said sample conduit for moving a sample of physiological liquid through said conduit and into said sample passage of said valve block, said plunger of said syringe being withdrawn from said seat when said valve block is in its first position for drawing reagent into said syringe seat through said reagent conduit, said pump means supplying a sample of physiological liquid to said sample passage, and said syringe being moved into said syringe seat when said valve block is in its second position for forcing reagent through said mixture conduit and mixing the reagent with sample in said sample passage to form the mixture and propelling the mixture through said mixture conduit into said cuvette.

12. An instrument according to claim 11, wherein said sample pump means comprises a suction pump, a spent sample container connected to said suction pump and disposed in said sample conduit, the instrument including additional dispenser means distributed along said sample conduit, a first sample sensor disposed in said conduit before the first of said dispenser means and a second sensor disposed in said conduit after the last of said dispenser means, a valve in said sample conduit between said spent sample container and said suction pump connected to said control circuit means for disconnecting said suction pump from said sample conduit, a peristaltic pump in said sample conduit between said last dispenser means and said spent sample container for manually drawing sample liquid from said sample container into said sample conduit.

13. An instrument according to claim 10, wherein said at least one cuvette comprises a transparent cuvette body comprising said frusto-conical shaped side wall, a drive shaft connected to said cuvette body axially aligned with said axis, a pulley fixed to said shaft, said drive means comprising a motor, a belt connected to said motor driven by said motor, said belt engaged about said pulley for rotating said cuvette body about said axis.

14. An instrument according to claim 13, further including an analyzer housing disposed about said cuvette body including a discharge canal communicating with the open top of said cuvette body, said canal receiving the mixture when said drive means are rotated to expel the mixture from said cuvette body by centrifugal force, a heating fluid cavity in said analyzer housing for receiving a heated fluid, a mixture conduit extending between said dispenser means and said cuvette for dispensing the mixture into said cuvette, said mixture conduit including a coil portion disposed in said heating cavity for absorbing heat from said heating fluid before the mixture is deposited in said cuvette, said analyzer housing including a cover member having an inclined inner surface facing the top opening of said cuvette for providing a path for condensates expelled from said cuvette to said discharge canal.

* * * * *